(12) United States Patent
Draper et al.

(10) Patent No.: US 12,239,828 B1
(45) Date of Patent: Mar. 4, 2025

(54) ATTACHMENT MECHANISM, MODULE AND ASSEMBLY HEREWITH

(71) Applicant: Sanofi, Paris (FR)

(72) Inventors: Paul Richard Draper, Warwick (GB); Aidan Michael O'Hare, Warwick (GB); Robert Frederick Veasey, Warwick (GB); Andrew Wallace, Warwick (GB)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 18/620,501

(22) Filed: Mar. 28, 2024

(51) Int. Cl.
*A61M 5/31* (2006.01)
*A61M 5/315* (2006.01)

(52) U.S. Cl.
CPC .... *A61M 5/31568* (2013.01); *A61M 5/31551* (2013.01); *A61M 2205/3327* (2013.01); *A61M 2205/3375* (2013.01)

(58) Field of Classification Search
CPC .................................................. A61M 5/31568
See application file for complete search history.

(56) References Cited

U.S. PATENT DOCUMENTS

| | | |
|---|---|---|
| 5,693,027 A | 12/1997 | Hansen et al. |
| 6,663,602 B2 | 12/2003 | Moller |
| 7,241,278 B2 | 7/2007 | Moller |
| 9,937,294 B2 | 4/2018 | Quinn et al. |
| 2008/0306446 A1 | 12/2008 | Markussen |
| 2009/0054839 A1 | 2/2009 | Moller et al. |
| 2009/0216182 A1 * | 8/2009 | Lauchard ............. H03K 17/955 604/65 |
| 2021/0330891 A1 * | 10/2021 | Byerly .................... A61M 5/20 |
| 2023/0248906 A1 | 8/2023 | Despa et al. |

FOREIGN PATENT DOCUMENTS

| | | |
|---|---|---|
| EP | 0118250 A2 | 9/1984 |
| EP | 1570876 B1 | 12/2009 |
| EP | 2814547 B1 | 7/2015 |
| EP | 2890434 B1 | 4/2020 |
| WO | WO 2004/068820 A2 | 8/2004 |
| WO | WO 2004/078239 A1 | 9/2004 |
| WO | WO 2005/018629 A1 | 3/2005 |
| WO | WO 2005/018721 A1 | 3/2005 |
| WO | WO 2006/003388 A2 | 1/2006 |

(Continued)

OTHER PUBLICATIONS

Hamers-Casterman et al., "Naturally occurring antibodies devoid of light chains," Nature, Jun. 3, 1993, 363(6428):446-448.

(Continued)

*Primary Examiner* — Courtney B Fredrickson
(74) *Attorney, Agent, or Firm* — Fish & Richardson P.C.

(57) ABSTRACT

The present disclosure is generally directed to an attachment mechanism suitable for attaching a module to an object, e.g. to a portion of a drug delivery device. Further, the disclosure is directed to an electronic system, e.g. an electronic add-on module, which is configured to be, e.g. releasably, attached to a drug delivery device as well as an assembly including the electronic add-on module as well as the drug delivery device. The attachment mechanism may include at least one attachment member with a longitudinal axis, an adhesive distal end surface and an opposite adhesive proximal end surface.

11 Claims, 3 Drawing Sheets

(56) References Cited

FOREIGN PATENT DOCUMENTS

| WO | WO 2006/030220 A1 | 3/2006 | | |
|---|---|---|---|---|
| WO | WO 2009/132777 A1 | 11/2009 | | |
| WO | WO 2014/033195 A1 | 3/2014 | | |
| WO | WO 2016/198516 A1 | 12/2016 | | |
| WO | WO 2019/145415 A1 | 8/2019 | | |
| WO | WO-2022018106 A1 * | 1/2022 | ........ | A61M 5/31546 |
| WO | WO-2022018107 A1 * | 1/2022 | ........ | A61M 5/31546 |
| WO | WO 2023/059577 A1 | 4/2023 | | |
| WO | WO-2024083511 A1 * | 4/2024 | | |

OTHER PUBLICATIONS

Holt et al., "Domain antibodies: proteins for therapy," Trends in Biotechnology, Nov. 2003, 21(11):484-490.

International Organization of Standards, "Self adhesive tapes: Determination of peel adhesion properties," ISO 29862:2018(E), May 2018, 22 pages.

Muyldermans, "Single domain camel antibodies: current status," Reviews in Molecular Biotechnology, Jun. 2001, 74(4):277-302.

Needle-based injection systems for medical use Requirements and test methods, Part 1: Needle injection systems, ISO 11608-1:2014(E), Third Edition, Switzerland, ISO, Dec. 15, 2014, pp. 1-13.

Ward et al., "Binding activities of a repertoire of single immunoglobulin variable domains secreted from *Escherichia coli*," Nature, Oct. 12, 1989, 341:544-546.

* cited by examiner

ATTACHMENT MECHANISM, MODULE AND ASSEMBLY HEREWITH

TECHNICAL FIELD

The present disclosure is generally directed to an attachment mechanism suitable for attaching for example a module to an object which may have an essentially circular or annular end surface, e.g. to a portion of a drug delivery device. Further, the disclosure is directed to an electronic system, e.g. an electronic add-on module, which is configured to be, e.g. releasably, attached to a drug delivery device as well as an assembly comprising the electronic add-on module as well as the drug delivery device.

BACKGROUND

Electronic add-on modules may be used attached on to a drug delivery device, e.g. a pentype injection device. Such drug delivery devices often comprise a housing with a container configured to receive a drug or a cartridge filled with a drug, a dose setting unit comprising a dose dial user interface, e.g. a dial grip, at least rotationally moveable with respect to the housing during dose setting and an injection user interface, e.g. a dose button, at least axially moveable with respect to the housing for causing dose dispensing, and a dose delivery unit comprising a plunger at least axially moveable with respect to the housing during dose dispensing.

Electronic add-on modules for releasable attachment to drug delivery devices may be used to measure relevant data with respect to dose setting and/or dose dispensing. Due to the different dimensions and working principles of injection devices, especially regarding dose dial user interfaces and injection user interfaces, such add-on modules can be tailored to fit to one specific drug delivery device. This requires providing different modules for different devices.

An example of an electronic add-on module is described in WO 2016/198516 A1 which comprises a sleeve-like portion to be positioned over a dosage knob or dial grip of an injection device. A resilient padding is provided on the inner surface of the sleeve-like portion. The padding deforms to accommodate the dosage knob within the cavity of the sleeve-like portion.

Further, a monitoring device for attachment to an injection device is described in WO 2019/145415 A1. This add-on device comprises a coupling element adapted for accommodating the push button and the selector of an insulin pen. In order to adapt to the specific form of any dose selector, the coupling element comprises a gasket with an inner orifice, whose inner surface is similar to the external surface of the selector, such that it can slide along it and embrace it achieving a firm attachment thereto. By employing different designs for the gasket, the device can be used with any available model of drug pen. The gasket is a removable element which can be detached from the coupling element for example, to be interchanged with other gaskets for the adaptation of the device for its coupling to different models of drug pens.

SUMMARY

The present disclosure relates to an improved attachment mechanism, an improved electronic add-on module suitable to be used with various different drug delivery devices and an improved assembly comprising a drug delivery device and such an electronic add-on module.

In the field of dose recording modules for injection devices, it is advantageous to attach the module on the proximal end of the injection device so that the small cylindrical form is maintained, which is important for comfortable use of the device. This means it is advantageous to attach the module to either the dose dial grip of the injection device or the dose button. If the module is attached to the dose dial grip then this does have the downside of adding diametric size to the assembly, and furthermore in many injection devices the dose dial grip rotates during dosing and therefore the users hand needs to be clear of that part of the module to prevent blocking. Therefore, it is advantageous to attach a module to the dose button of the device. However, for most injection devices the dose button does not have suitable features to form a purely mechanical attachment. Therefore the present disclosure provides an attachment mechanism suitable to attach a module to the dose button of a drug delivery device.

An attachment mechanism is configured for attaching a module to an object that may have an essentially circular or annular end surface, like an, e.g. cylindrical, drug delivery device or a portion thereof, may comprise at least one attachment member with a longitudinal axis, a distal end surface and an opposite proximal end surface. Attachment of a module or the like to a drug delivery device or the like may be effected by means of the distal end surface being an adhesive surface and the proximal end surface being an adhesive surface, for example a peelable adhesive surface. The attachment member may have a substantially circular or annular discshape with a thickness in the direction of the longitudinal axis being small compared with the extension in a plane perpendicular to the longitudinal axis. For example, the attachment member may be substantially circular with a thickness of 0.05 mm to 2.5 mm, preferably less than 1.0 mm, and a diameter of 4 mm to 20 mm, preferably about 12 mm to 15 mm.

According to an aspect of the present disclosure, the module is reusable and can be used across multiple injection devices, therefore the attachment mechanism is intended to be also detachable. For example, the user may be supplied with multiple attachment members to use across the lifetime of the module with multiple injection devices. The user would apply the attachment member to the module and apply the module to the injection device or vice versa apply the attachment member to the injection device and then attach the module. To remove the module for use with another injection device the user would "peel" the module from the injection device.

The attachment mechanism of the present disclosure may comprise or may consist of one or more layers of a pressuresensitive adhesive (PSA), i.e. an adhesive that will stick with application of pressure without the need for a solvent or heat for activation, for example on the basis of an elastomer, e.g. based on acrylics, which can have sufficient tack on their own. The attachment mechanism of the present disclosure may comprise or may consist of an attachment member in the form of a pressuresensitive adhesive tape which is an adhesive tape. The attachment member may be a selfadhesive tape comprising a substrate and one or more layers of a pressuresensitive adhesive.

According to an aspect of the present disclosure, the attachment member may be a doublesided adhesive tape which has adhesive on both sides. As an optional feature of the attachment member, the proximal surface for attachment to the module may have a lower adhesion force than the distal surface for attachment to the injection device. In this way when the user peeled the module from the injection device, the proximal surface would preferentially unstick over the distal surface to ensure that the attachment member remained attached to the injection device and was disposed of with the injection device leaving the module clear and ready to attach a new attachment member for the next injection device. For example, the proximal end surface has a peel adhesion (measured according to ISO 29862:2018) which is at least 10%, e.g. between 15% and 30%, preferably about 25%, lower than the peel adhesion of the distal end surface. In addition or as an alternative, the proximal end surface may have a peel adhesion (measured according to ISO 29862:2018) of 2 N/cm to 10 N/cm, preferably about 5 N/cm.

According to a further aspect of the present disclosure, the proximal end surface of the dose button of the drug delivery device and/or the distal end surface of the module may be shaped and/or provided with surface profiles resulting in an increased contact area between the attachment member and the proximal end surface of the dose button of the drug delivery device than the contact area between the attachment member and the distal end surface of the module. This may contribute in reduced peeling forces for detachment of the attachment member from the module than from the dose button.

According to a still further example of the present disclosure, the attachment member may comprise a deformable and/or viscoelastic substrate layer, e.g. a foam substrate, interposed between the two adhesive surfaces, i.e. between the distal end surface and the proximal end surface. A suitable foam may be an acrylic foam. Such a deformable and/or viscoelastic substrate layer may be suitable to increase the contact area in case of not perfectly flat surfaces abutting the attachment member. In other words, the attachment member may be in full contact with the respective surface, even if the surface has recesses, protrusions and/or is curved. Instead of an attachment member having a substrate layer interposed between two adhesive layers, the whole attachment member may be a single layer of an adhesive material, e.g. an acrylic foam. In this case, the opposite sides of the foam constitute the adhesive the distal end surface and the adhesive proximal end surface.

The attachment mechanism may be used in or with an electronic add-on module which may be, e.g. releasably, attached to the drug delivery device by frictional, elastic and/or form fit engagement with the releasable gripping portion. A module according to the present disclosure comprises an attachment mechanism as defined above. An assembly according to the present disclosure comprises a drug delivery device and an electronic add-on module configured for releasable attachment to the drug delivery device.

Drug delivery devices may comprise at least a housing with a container configured to receive a drug or a cartridge filled with a drug. Further, the drug delivery device may comprise a dose setting unit and a dose delivery unit. Suitable drug delivery devices to be used with a mechanism or module according to the present disclosure are described e.g. in WO 2004/078239 A1, EP 1 570 876 B1, EP 2 814 547 B1, EP 2 890 434 B1, WO 2005/018721 A1, WO 2009/132777 A1, WO 2014/033195 A1, U.S. Pat. Nos. 5,693,027 A, 6,663,602 B2, 7,241,278 B2 or 9,937,294 B2. In addition to manually driven devices, the module may be used with spring driven devices as described in US 2008/306446 A1 or US 2009/054839 A1. However, the present disclosure is not limited to these examples of drug delivery devices. Rather, other drug delivery devices with a stationary and/or operable portion having an e.g. substantially cylindrical shape may be used with the module. For example, the drug delivery devices may comprise a user interface for selecting and/or dispensing a fixed or variable dose of a drug.

The dose setting unit may comprise a dose dial user interface, e.g. a dose dial grip, which is, at least rotationally, e.g. helically, moveable with respect to the housing during dose setting and an injection user interface at least axially moveable with respect to the housing for causing dose dispensing. The injection user interface may be a separate component part, e.g. a dose button, which may be displaced relative to the dose dial user interface for causing dose dispensing. As an alternative, the dose dial user interface and the injection user interface may be portions of one single component part, e.g. a combined dose dial and injection knob. The electronic add-on module may comprise or define an auxiliary injection user interface configured to apply pressure onto the injection user interface of the drug delivery device when attached to the drug delivery device.

According to an independent aspect of the present disclosure, the module may comprise an electrical power source, e.g. a battery or a rechargeable cell, a printed circuit board assembly (PCBA), e.g. comprising and/or forming a control unit, a sensor arrangement, for example an acoustic sensor arrangement comprising e.g. at least one microphone, configured to detect a relative rotational movement between at least two component parts of the drug delivery device, a communication unit for communicating with another device, e.g. for wireless transfer of data, and/or a switch arrangement, e.g. for turning the electronic module on and off and/or for waking the module or its components from a sleeping mode or a low power consumption mode. In an example of the present disclosure, the main housing may encase the electrical power source, the printed circuit board assembly, the sensor arrangement, the communication unit, and/or the switch arrangement. For example, the sensor arrangement comprises at least one microphone connected to the printed circuit board assembly. According to a further independent aspect of the present disclosure, the sensor arrangement may be configured to detect click sounds generated by a relative rotational movement between at least two component parts of the drug delivery device wherein the electronic module is configured to determine an amount of dose selected and/or dispensed on the basis of the click sounds detected by the sensor arrangement.

In the switch arrangement of the electronic add-on module the proximal actuation surface may be an elastically deformable surface with a snap dome type switch positioned beneath the proximal actuation surface. This example is especially useful in order to activate the module at the start of an injection. For example, the switch is arranged such that when the user applies force to initiate a dispense the deformable surface first deforms and activates the switch. The switch activates the electronic circuit and a sensor, e.g. a microphone which counts the clicks from the mechanism that represents units delivered.

As an alternative (or in addition), the proximal actuation surface may comprise electrodes forming a capacitive switch. In this alternative example, the switch arrangement is effectively zero force, or contact sensitive. This has the benefit that the dose counting electronics are ready to start at the beginning of a dose. This avoids the risk with the above example that the force required to deflect the deformable surface could be greater than the force required to initiate the dose dispense within the injection device.

According to a further aspect of the present disclosure, when the electrical power source comprises a rechargeable battery, the electrodes of the proximal actuation surface may form connectors for charging the rechargeable battery.

An assembly according to the present disclosure comprises a drug delivery device and an electronic add-on module configured for releasable attachment to the drug delivery device.

Preferably, the drug delivery device comprises: a device housing with a container configured to receive a drug or a cartridge filled with a drug, a dose setting unit comprising a dose dial user interface at least rotationally moveable with respect to the device housing during dose setting and an injection user interface at least axially moveable with respect to the device housing for causing dose dispensing, and a dose delivery unit comprising a plunger at least axially moveable with respect to the device housing during dose dispensing.

Although not required in the context of the present disclosure, the drug delivery device may optionally comprise further components such as a drive sleeve, a number sleeve, a clutch, a cap, a needle, a spring, a lead screw or the like, interacting with the dose button, the dose dial grip, the drive sleeve, the plunger and/or the housing, for example as disclosed in WO 2004/078239 A1. However, the present disclosure is not limited to the drug delivery device of WO 2004/078239 A1. Other suitable drug delivery devices to be used with such a module may comprise a dial grip for selecting a variable dose and a separate dose button for initiating or performing dose dispensing, e.g. as described in EP 1 570 876 B1, EP 2 814 547 B1, EP 2 890 434 B1, WO 2009/132777 A1, U.S. Pat. No. 6,663,602 B2, U.S. Pat. No. 7,241,278 B2 or U.S. Pat. No. 9,937,294 B2. In addition, other suitable drug delivery devices to be used with such a module may comprise a single knob forming a dial grip for selecting a variable dose and a dose button for initiating or performing dose dispensing, e.g. as described in WO 2005/018721 A1 or WO 2014/033195 A1. Still further, the drug delivery device may be a spring driven device as described in US 2008/306446 A1 or US 2009/054839 A1.

If the drug delivery device has a similar working principle as in the example of WO 2004/078239 A1, during dose setting components of the drug delivery device may perform the following movements. A housing may be stationary and may be used as a reference system for the further movements of other components. A plunger may be stationary and may be guided in a housing thread. A drive sleeve may be provided rotationally coupled to the dose dial grip during dose setting and rotationally constrained to the housing during dose dispensing. In other words, the drive sleeve may be guided in the housing to perform a purely axial movement during dose dispensing. The drive sleeve may perform a helical movement, i.e. a combined axial and rotational movement, and may be in threaded engagement with the plunger. A dial grip may perform a helical movement. A dose button may be free to rotate but axially constrained to the drive sleeve. For example, the dose button may be axially retained to the drive sleeve by a clutch. An optional clutch may perform a helical movement and may couple a number sleeve to the drive sleeve. An optional clutch spring may perform an axial movement and may be guided in housing splines and may click over clutch teeth. An optional number sleeve may be permanently fixed on the dial grip and may perform a helical movement and may be guided in a housing thread. An optional last dose nut may perform a helical movement on a drive sleeve track of the drive sleeve and may be rotationally constrained to the housing. Hence, the last dose nut may perform axial movement relative to the housing and a helical movement with respect to the drive sleeve.

During dose dispensing components of the drug delivery device may perform the following movements. The housing may remain stationary as a reference system for the further movements of other components. The plunger may perform a helical movement and may be guided in the housing thread. The drive sleeve may perform a pure axial movement and may be in threaded engagement with the plunger. The dose dial grip may perform a helical movement and may be permanently fixed on the number sleeve. The dose button may perform an axial movement if coupled to the drive sleeve and/or the clutch. The optional clutch may perform pure axial movement and may decouple the number sleeve from the drive sleeve. The optional clutch spring may perform pure axial movement and may be rotationally constrained to the clutch due to a pressure applied to the dose button. The optional number sleeve may perform a helical movement and may be guided in the housing thread. The optional last dose nut may maintain its axial position on the drive sleeve track and may be rotationally constrained to the housing.

In an assembly according to the present disclosure, when the module is attached to the injection user interface of the drug delivery device, the dose button may be attached to the module in a releasable manner by means of the attachment member, e.g. a selfadhesive tape or double-sided adhesive tape.

According to an independent aspect of the present disclosure, the assembly comprises a drug delivery device having a clicker mechanism generating an acoustic feedback signal during specific use conditions, e.g. at least during dose setting. Such a feedback signal may be detected by the electronic module and the module may determine an amount of dose selected and/or dispensed. For example, the clicker mechanism may generate one clicking sound for every IU dispensed, like e.g. in WO 2004/078239 A1, WO 2014/033195 A1, WO 2005/018721 A1 or EP 1 570 876 B1.

The electronic add-on module may be an electronic dose recording system for determining, storing and/or transmitting data indicative of at least a condition of the drug delivery device or its use. For example, the system may detect if the drug delivery device is switched between a dose setting mode and a dose dispensing mode and vice versa. In addition or as an alternative, the system may detect if a dose is set and/or if a dose is dispensed. Still further, the system may detect the amount of dose selected and/or the amount of dose dispensed. Preferably, the electronic addon module is configured such that it may be switched from a first state having lower energy consumption into a second state having higher energy consumption. This may be achieved by operation of the electronic add-on module, especially by actuating the microswitch. As an alternative, the module may be provided with a wake up functionality which does not require a separate actuation action. The first state may be a sleeping mode and the second mode may be a detection and/or communication mode. As an alternative, an electronic control unit may issue a command, e.g. a signal, to another unit of the electronic dose recording system such that this unit is switched on or rendered operational.

The electronic add-on module may further comprise a communication unit for communicating with another device, e.g. a wireless communications interface for communicating with another device via a wireless network such as Wi-Fi or Bluetooth, or even an interface for a wired communications link, such as a socket for receiving a Universal Serial Bus (USB), miniUSB or microUSB connector. Preferably, the electronic add-on module comprises an RF, Wi-Fi and/or Bluetooth unit as the communication unit. The communication unit may be provided as a communication interface between the electronic addon module and the exterior, such as other electronic devices, e.g. mobile phones, personal computers, laptops and so on. For example, dose data may be transmitted by the communication unit to the external device. The dose data may be used for a dose log or dose history established in the external device.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short or longterm storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about 4° C. to about 4° C.). In some instances, the drug container may be or may include a dualchamber cartridge configured to store two or more components of the pharmaceutical formulation to be administered (e.g., an API and a diluent, or two different drugs) separately, one in each chamber. In such instances, the two chambers of the dualchamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (antidiabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including noncodeable amino acids, or amino acids, including noncodeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victo-za®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin. Examples of polysaccharides include a glucosaminoglycane, a hyaluronic acid, a heparin, a low molecular weight heparin or an ultralow molecular weight heparin or a derivative thereof, or a sulphated polysaccharide, e.g. a polysulphated form of the above-mentioned polysaccharides, and/or a pharmaceutically acceptable salt thereof. An example of a pharmaceutically acceptable salt of a polysulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigenbinding portions of immunoglobulin molecules include F(ab) and F(ab')2 fragments, which retain the ability to bind antigen. The antibody can be polyclonal, monoclonal, recombinant, chimeric, deimmunized or humanized, fully human, nonhuman, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigenbinding molecule based on tetravalent bispecific tandem immunoglobulins (TBTI) and/or a dual variable region antibodylike binding protein having crossover binding region orientation (CODV).

The terms "fragment" or "antibody fragment" refer to a polypeptide derived from an antibody polypeptide molecule (e.g., an antibody heavy and/or light chain polypeptide) that does not comprise a fulllength antibody polypeptide, but that still comprises at least a portion of a fulllength antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (singlechain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, small modular immunopharmaceuticals (SMIP), bindingdomain immunoglobulin fusion proteins, camelized antibodies, and immunoglobulin single variable domains. Additional examples of antigenbinding antibody fragments are known in the art.

The term "immunoglobulin single variable domain" (ISV), interchangeably used with "single variable domain", defines immunoglobulin molecules wherein the antigen binding site is present on, and formed by, a single immunoglobulin domain. As such, immunoglobulin single variable domains are capable of specifically binding to an epitope of the antigen without pairing with an additional immunoglobulin variable domain. The binding site of an immunoglobulin single variable domain is formed by a single heavy chain variable domain (VH domain or VHH domain) or a single light chain variable domain (VL domain). Hence, the antigen binding site of an immunoglobulin single variable domain is formed by no more than three CDRs.

An immunoglobulin single variable domain (ISV) can be a heavy chain ISV, such as a VH (derived from a conventional fourchain antibody), or VHH (derived from a heavy-chain antibody), including a camelized VH or humanized VHH. For example, the immunoglobulin single variable domain may be a (single) domain antibody, a "dAb" or dAb or a Nanobody® ISV (such as a VHH, including a humanized VHH or camelized VH) or a suitable fragment thereof. [Note: Nanobody® is a registered trademark of Ablynx N.V.]; other single variable domains, or any suitable fragment of any one thereof.

"VHH domains", also known as VHHs, VHH antibody fragments, and VHH antibodies, have originally been described as the antigen binding immunoglobulin variable domain of "heavy chain antibodies" (i.e., of "antibodies devoid of light chains"; Hamers-Casterman et al. 1993 (Nature 363: 446-448). The term "VHH domain" has been chosen in order to distinguish these variable domains from the heavy chain variable domains that are present in conventional 4-chain antibodies (which are referred to herein as "VH domains") and from the light chain variable domains that are present in conventional 4-chain antibodies (which are referred to herein as "VL domains"). For a further description of VHH's, reference is made to the review article by Muyldermans 2001 (Reviews in Molecular Biotechnology 74: 277-302).

For the term "dAb's" and "domain antibody", reference is for example made to Ward et al. 1989 (Nature 341: 544), to Holt et al. 2003 (Trends Biotechnol. 21: 484); as well as to WO 2004/068820, WO 2006/030220, WO 2006/003388. It should also be noted that, although less preferred in the context of the present disclosure because they are not of mammalian origin, single variable domains can be derived from certain species of shark (for example, the socalled "IgNAR domains", see for example WO 2005/18629).

The terms "Complementarity determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

An example drug delivery device may involve a needle-based injection system as described in Table 1 of section 5.2 of ISO 116081:2014(E). As described in ISO 116081:2014(E), needlebased injection systems may be broadly distinguished into multidose container systems and singledose (with partial or full evacuation) container systems. The container may be a replaceable container or an integrated nonreplaceable container.

As further described in ISO 11608-1:2014(E), a multidose container system may involve a needlebased injection device with a replaceable container. In such a system, each container holds multiple doses, the size of which may be fixed or variable (preset by the user). Another multidose container system may involve a needlebased injection device with an integrated nonreplaceable container. In such a system, each container holds multiple doses, the size of which may be fixed or variable (preset by the user).

As further described in ISO 11608-1:2014(E), a single-dose container system may involve a needlebased injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014(E), a singledose container system may involve a needlebased injection device with an integrated nonreplaceable container. In one example for such a system, each container holds a single dose, whereby the entire deliverable volume is expelled (full evacuation). In a further example, each container holds a single dose, whereby a portion of the deliverable volume is expelled (partial evacuation).

The terms "axial", "radial", or "circumferential" as used herein may be used with respect to a first longitudinal axis of the attachment mechanism, its sleeve, electronic add-on module, the first portion, the second portion, the drug delivery device, the cartridge, the housing, the cartridge holder or the assembly of the drug delivery device and the electronic add-on module, e.g. the axis which extends through the proximal and distal ends of the cartridge.

"Distal" is used herein to specify directions, ends or surfaces which are arranged or are to be arranged to face or point towards dispensing end of the electronic add-on module or the drug delivery device or components thereof and/or point away from, are to be arranged to face away from or face away from the proximal end. On the other hand, "proximal" is used to specify directions, ends or surfaces which are arranged or are to be arranged to face away from or point away from the dispensing end and/or from the distal end of the electronic add-on module or the drug delivery device or components thereof. The distal end may be the end closest to the dispensing and/or furthest away from the proximal end and the proximal end may be the end furthest away from the dispensing end. A proximal surface may face away from the distal end and/or towards the proximal end. A distal surface may face towards the distal end and/or away from the proximal end. The dispensing end may be the needle end where a needle unit is or is to be mounted to the device, for example. Similarly, a distal element compared to a proximal element is located closer to the dispensing end than to the proximal end. Furthermore, when the electronic add-on module is considered alone, the term "distal" may be used with regard to the more distal end of the electronic add-on module, which is located closer to the dispensing end of the drug delivery device when attached to the drug delivery device, and the term "proximal" may be used with regard to the proximal end of the electronic add-on module, which is located further away from the dispensing end of the drug delivery device when attached to the drug delivery device.

In the following, nonlimiting, examples of the attachment mechanism, the electronic add-on module, the drug delivery device and the assembly of the drug delivery device and the electronic add-on module are described in more detail by making reference to the drawings, in which:

BRIEF DESCRIPTION OF THE FIGURES

In the Figures, identical elements and components as well as identical elements and components in different examples or embodiments, i.e. elements and components acting identical or provided for the same purposes but belong to different examples, are provided with the same reference signs.

DETAILED DESCRIPTION

Figures 1, 2:
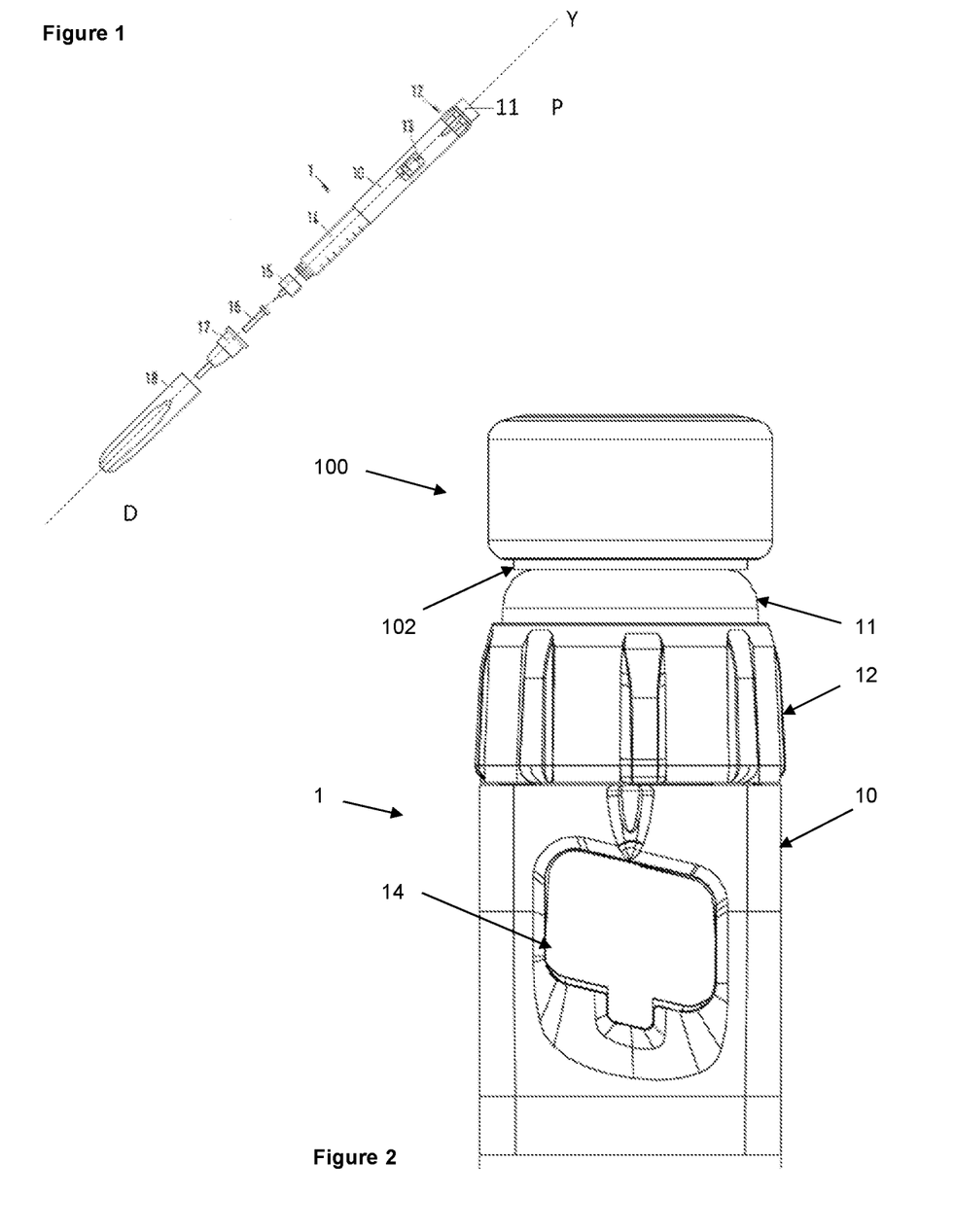
FIG. 1 shows a drug delivery device.
FIG. 2 shows the proximal end of a drug delivery device with a module attached by means of an attachment mechanism according to the present disclosure.

FIG. 1 shows an exploded view of an exemplary medicament or drug delivery device 1. The drug delivery device 1 is a pentype injector comprising a housing 10 in which a drive mechanism for dose setting and dose dispensing is arranged. The drug delivery device 1 extends from a distal point to a proximal direction P or from a proximal point to a distal direction D along a longitudinal axis Y of the drug delivery device 1. In order to set a dose for delivery a user may rotate or dial a dose dial grip 12 with respect to the housing 10, wherein the dose dial grip 12 is arranged at or near a proximal end of the housing 10. During dose setting the dose dial grip 12 may perform a helical movement, i.e. a combined axial and rotational movement, or may perform pure rotational movement.

The drive mechanism of the drug delivery device 1 may comprise a plunger, a drive sleeve (partially visible through window 13 in FIG. 1), a clutch, a clutch spring, a number sleeve, a last dose nut and so on, which may move during dose setting and/or dose dispensing. Although not all of these components are shown in detail, for example, the drive mechanisms disclosed in EP 1 570 876, EP 2 814 547, U.S. Pat. No. 9,937,294 B2 or WO 2004/078239 A1 represent suitable drive mechanisms for the present disclosure.

Once the dose is set by means of the dose dial grip 12, the user may press a dose button 11 arranged at the proximal end of the drug delivery device 1 in the distal direction D in order to dispense the dose. When pressing the dose button 11, the user applies a force directed towards the proximal end of the drug delivery device 1, wherein the force moves the dose button 11 in the distal direction of the pen and parallel to the longitudinal axis Y. This axial movement of the dose button 11 releases the drive mechanism for example by decoupling a number sleeve from the drive sleeve, wherein irrespective of which component of the drug delivery device 1 performs a rotational movement during dose delivery, the dose dial grip 12 is coupled to a respective component in order to perform a rotational movement during dose delivery.

This rotational movement of the dose dial grip 12 during dose delivery may generate an acoustic signal which in turn may be used to determine, for example, the actual dose delivered by means of an electronic add-on module 100 as shown in in FIGS. 3 and 4 and described here below.

The exemplary drug delivery device 1 shown in FIG. 1 comprises in addition to the dose dial grip 12 and the dose button 11 an optional dosage window 13, a container 14, and a needle hub 15. The set dose may be displayed via the dosage window 13. The container 14 may be filled directly with a drug, for example insulin, or may be configured to receive a cartridge and thus act as a cartridge holder. The needle hub 15 may be affixed to the container or the receptacle. During dose dispensing the drug is dispensed through the needle. The needle may be protected by an inner needle cap 16 and/or an outer needle cap 17. In addition, the needle may be protected by an outer cap 18.

In order for an electronic add-on module 100 to be functionally attached to a drug delivery device 1, i.e. attached and usable, either the drug delivery device 1 can be adapted to the electronic add-on module 100 or, conversely, the electronic add-on module 100 can be adapted to the drug delivery device 1. Regardless of this, the drug delivery device 1 as well as the electronic add-on module 100 may have different examples, wherein the further description with respect to the drug delivery device 1 essentially deals with the dose button 11 and the dose dial grip 12.

Figure 3:
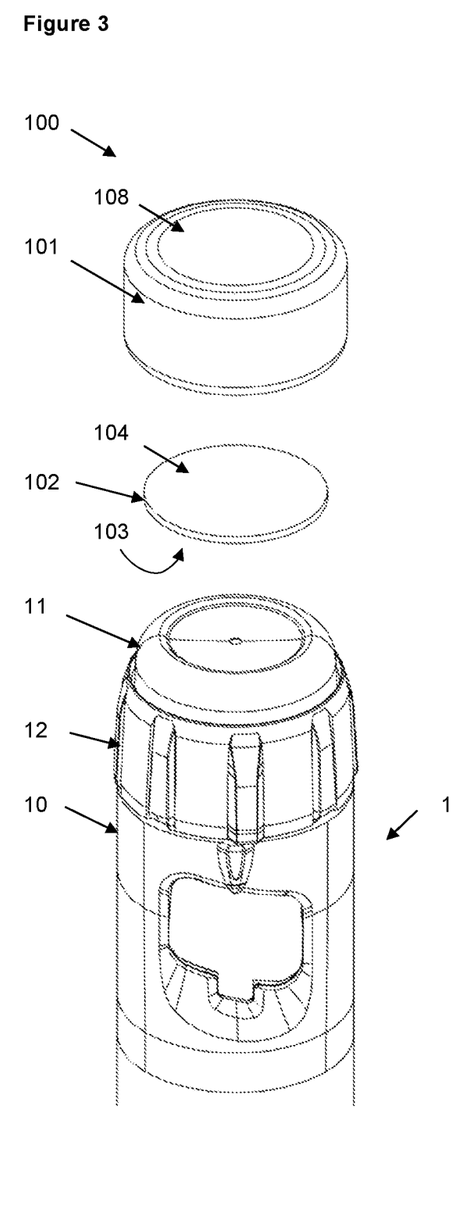
FIG. 3 shows an exploded view of FIG. 2.
Figure 4:
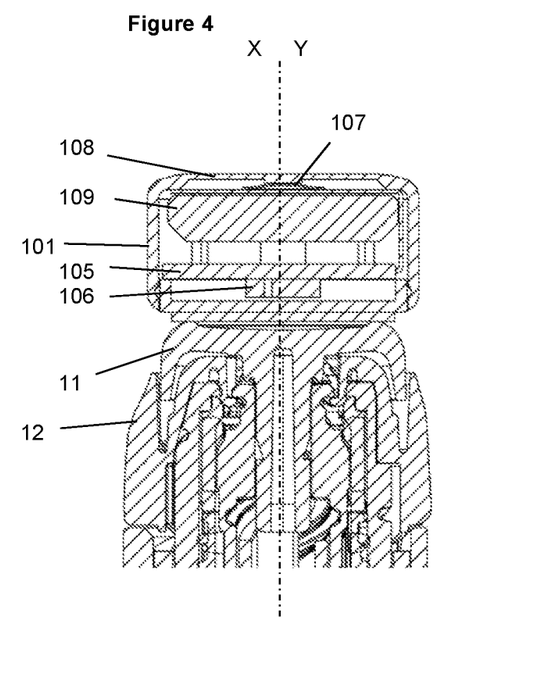
FIG. 4 shows a sectional view of FIG. 2.

FIGS. 2 to 4 show an exemplary embodiment of an electronic add-on module 100 suitable for releasable attachment to a user interface of drug delivery device 1. The module 100 comprises a main outer housing 101 defining a longitudinal axis X coinciding with the longitudinal axis Y of the drug delivery device when attached to each other.

In this disclosure the module 100 is attached to a standard injection device, e.g. the drug delivery device 1, via an attachment member 102. The attachment member 102 is arranged with two adhesive surfaces, a distal end surface 103 and an opposite proximal end surface 104. One surface, namely the proximal end surface 104, is arranged to interface with a distal end surface of the module 100, whilst the other surface, namely the distal end surface 103, is arranged to interface with a proximal surface of the injection device, and specifically the dose button 11 of the injection device 1.

The attachment member 102 may be for example self-adhesive tape or double-sided adhesive tape. The user may be supplied with multiple attachment members 102 to use across the lifetime of the module 100 with multiple disposable injection devices 1. The user may apply the attachment member 102 to the module 100 and apply the module 100 to the injection device 1, or vice versa apply the attachment member 102 to the injection device 1 and then attach the module 100. To remove the module 100 for use with another injection device 1 the user may peel the module 100 from the injection device 1.

An optional feature of the attachment member 102 is that the proximal attachment surface 104 to the module 100 has a lower adhesion force or a lower peeling force than the distal attachment surface 103 to the injection device 100. In this way when the user peels the module from the injection device proximal surface 104 preferentially unsticks over distal surface 103 to ensure that the attachment member 102 remains attached to the injection device 1 and can be disposed of with the injection device 1 leaving the module 100 clear and ready to attach a new attachment member 102 for the next injection device 1. For example, the proximal surface 104 has a peel adhesion (measured according to ISO 29862:2018) which is at least 10%, preferably 25%, lower than the peel adhesion of the distal end surface 103. The proximal end surface 104 may have a peel adhesion (measured according to ISO 29862:2018) of e.g. 2 N/cm to 10 N/cm, preferably about 5 N/cm.

The module 100 is arranged as a substantially closed housing 101 which encases mechanical and/or electronic components. Arranged inside the housing 101, FIG. 4 shows an electronic circuit or PCBA 105 with at least one acoustic sensor 106, e.g. a microphone. The acoustic sensor 106 is arranged to detect click sounds from the injection device 1 and determine the dose dispensed. In order to achieve this a switch 107 is arranged to be activated at the start of an injection. In this embodiment the switch 107 is shown as a snap (or click dome) type switch and is positioned beneath an elastically deformable surface 108 of the module 100. This is arranged such that when the user applies force to initiate a dispense the deformable surface 108 first deforms and activates the switch 107. The switch 107 activates the electronic circuit and the acoustic sensor 106 which counts the clicks from the mechanism that represents units delivered. Also shown in the FIG. 4 is a power source 109.

As it is important that the dose counting electronics are ready to start at the beginning of a dose there may be a risk with the example above that, e.g. due to manufacturing tolerances of the deformable surface 108, the force required to deflect the deformable surface 108 may be greater than the force required to initiate the dose dispense within the injection device 1. Therefore a second example is shown in FIGS. 5 and 6 where the switching means is effectively zero force, or contact sensitive, thereby eliminating such an undesired scenario.

Figure 5:
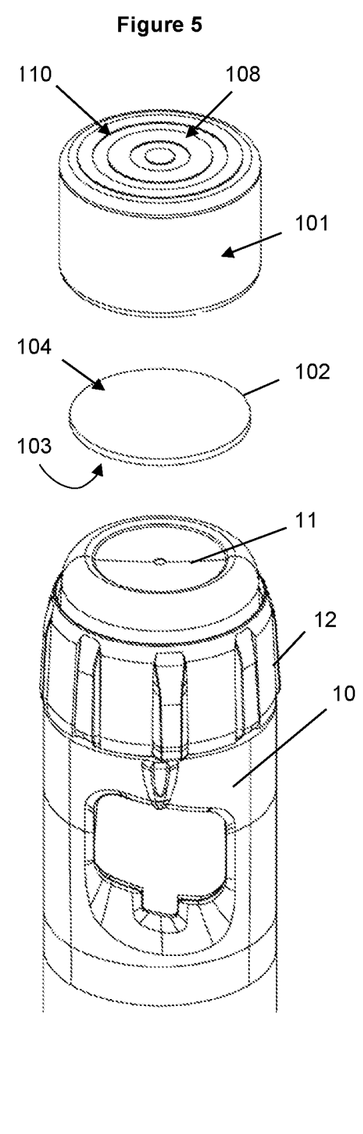
FIG. 5 shows an exploded view of a drug delivery device with a module attached by means of an attachment mechanism according to the present disclosure.
Figure 6:
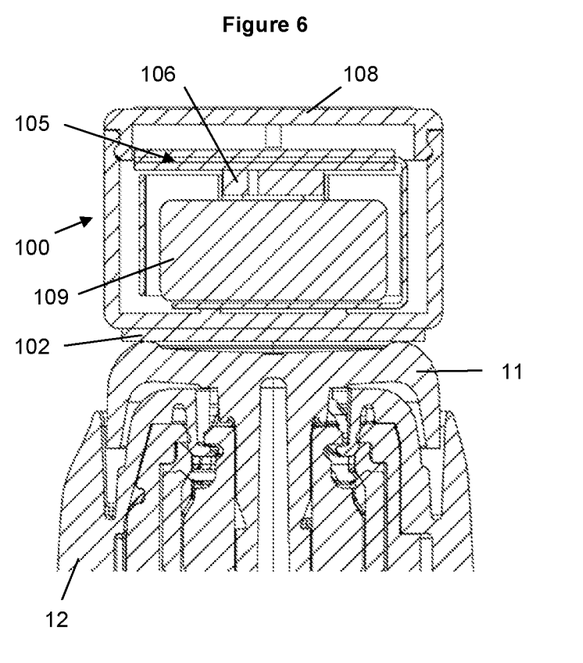
FIG. 6 shows a sectional view of FIG. 5.

In the example shown in FIGS. 5 and 6, the module 101 has electrodes 110 on a proximal surface 108. It is attached to the injection device 1 with the same attachment member 102 as the previous example. The attachment member 102 is arranged with two adhesive surfaces 103, 104. One surface 104 is arranged to interface with a distal surface of the module 100 whilst the other surface 103 is arranged to interface with a proximal surface of the injection device 1, and specifically the dose button 11 of the injection device.

This example of the module 100 is intended to operate by means of measuring the capacitance across the electrodes 110 and using that to determine when a user's finger or thumb is in contact with the proximal surface 108 of the module 100. It will use that determination as a switch input and trigger dose counting to occur whilst the thumb or finger is in contact. The arrangement of electrodes 110 may not be exactly as shown, many possible implementations of capacitive electrodes 110 are commonly used.

In addition, the electrodes 110 may be used for recharging of the power source 109.

Although not a restrictive element of the example, in this case the arrangement inside the module 100 may be slightly different to the first example. It may be the case that a capacitive switch element will draw more current during standby as it has to remain with a certain amount of activity in order to be able to detect the capacitance change. This may mean that it is more appropriate to include a rechargeable battery as power source 109.

This example is therefore illustrated with an electronic circuit (PCBA) 105 and a rechargeable battery as power source 109 as well as the acoustic sensor 106, e.g. a microphone. An additional feature of this arrangement may be that the electrodes 110 may also form the electrical connectors for charging the battery.

In the depicted examples, the dose button 11 of the drug delivery device 1 is shown with a slightly curved proximal end face, thereby forming an annular bead protruding proximally from the radially inner portion of the proximal end surface. This results in a substantially annular contact surface for attachment of the module 100 by means of the attachment member 102. In other examples, the proximal end surface of the dose button 11 may have a different form, e.g. substantially flat, such that the contact surface for attachment of the module 100 by means of the attachment member 102 is rather circular.

Further, the depicted examples show the distal end surface of the module 100 substantially flat. As an alternative, the distal end surface of the module 100 may have a convex or concave curvature and/or may be provided with protrusions or recesses. According to an independent aspect of the present disclosure, the shape of the distal end surface of the module 100 may be adapted to have a smaller contact area with the attachment member 102 than the proximal end surface of the dose button 11. In this way, even if both adhesive surface 103, 104 would have the same adhesion force or peel adhesion, when the user peeled the module from the injection device proximal surface 104 preferentially unsticks over distal surface 103 to ensure that the attachment member 102 remains attached to the injection device 1 and can be disposed of with the injection device 1 leaving the module 100 clear and ready to attach a new attachment member 102 for the next injection device 1.

The attachment member 102 may comprise a deformable substrate layer, e.g. a foam substrate, interposed between the two adhesive surfaces, i.e. between the distal end surface 103 and the proximal end surface 104. A suitable substrate layer may be viscoelastic. For example the foam may be an acrylic foam. Such a deformable substrate layer may be suitable to use the whole proximal surface of the dose button 11. As an alternative, the whole attachment member 102 may be a single layer of an adhesive material, e.g. an acrylic foam, with the opposite sides of the foam being the adhesive the distal end surface 103 and the adhesive proximal end surface 104.

The attachment mechanism can be used to attach an electronic add-on module onto a pen injector dose button of any diameter within the design limits. The attachment member 102 allows attachment to dose buttons of different sizes (diameters) and shapes, which makes the attachment mechanism of the present disclosure compatible with any arbitrary dose button geometry. At the same time, the dial grip 12 of the drug delivery device 1 remains free which facilitates a good holding torque and does not interfere with the basic functionalities of the underlying injector, i.e., dose selection and correction.

REFERENCE NUMERALS 1 drug delivery device
10 housing
11 dose button
12 dose dial grip
13 display window
14 container
15 needle
16 inner needle cap
17 outer needle cap
18 outer cap
100 electronic add-on module
101 main housing
102 attachment member
103 distal end surface (adhesive surface)
104 proximal end surface (adhesive surface)
105 PCBA
106 sensor (microphone)
107 switch
108 deformable surface
109 power source (battery)
110 electrode
D distal direction
P proximal direction
X longitudinal axis (of the sleeve)
Y longitudinal axis (of the drug delivery device)

The invention claimed is:

1. An electronic add-on module configured to be releasably attached to a drug delivery device, wherein the electronic add-on module comprises:
   at least one attachment mechanism configured for releasably attaching the electronic add-on module to a portion of the drug delivery device,
   wherein the at least one attachment mechanism comprises:
      at least one attachment member with a longitudinal axis, a distal end surface, and an opposite proximal end surface,
      wherein the distal end surface is an adhesive surface and the proximal end surface is an adhesive surface; and
   a main housing with a distal attachment surface formed by the distal end surface of the at least one attachment mechanism and a proximal actuation surface, wherein the proximal actuation surface defines an auxiliary injection user interface configured to apply pressure onto an injection user interface of the drug delivery device,
   wherein the proximal actuation surface comprises electrodes forming a capacitive switch.

2. The electronic add-on module according to claim 1, wherein the main housing encases an electrical power source, a printed circuit board assembly, a sensor arrangement configured to detect a relative movement between at least two component parts of the drug delivery device, a communication unit for communicating with another device, and/or a switch arrangement.

3. The electronic add-on module according to claim 2, wherein the electrical power source comprises a rechargeable battery, and wherein the electrodes of the proximal actuation surface form connectors for charging the rechargeable battery.

4. The electronic add-on module according to claim 2, wherein the sensor arrangement comprises at least one microphone connected to the printed circuit board assembly.

5. The electronic add-on module according to claim 2, wherein the sensor arrangement is configured to detect click sounds generated by a relative rotational movement between at least two component parts of the drug delivery device, and wherein the electronic add-on module is configured to determine an amount of dose selected and/or an amount of dose dispensed based on the click sounds detected by the sensor arrangement.

6. The electronic add-on module according to claim 1, wherein the proximal actuation surface is an elastically deformable surface with a snap dome type switch positioned beneath the proximal actuation surface.

7. An assembly comprising:
  a drug delivery device comprising:
    a device housing with a container configured to receive a drug or a cartridge filled with a drug,
    a dose setting unit comprising a dose dial user interface at least rotationally moveable with respect to the device housing during dose setting and an injection user interface at least axially moveable with respect to the device housing for causing dose dispensing, and
    a dose delivery unit comprising a plunger at least axially moveable with respect to the device housing during dose dispensing; and
  an electronic add-on module releasably attached to the drug delivery device, wherein the electronic add-on module comprises
    at least one attachment mechanism configured for releasably attaching the electronic add-on module to a portion of the drug delivery device,
    wherein the at least one attachment mechanism comprises:
      at least one attachment member with a longitudinal axis, a distal end surface, and an opposite proximal end surface,
      wherein the distal end surface is an adhesive surface and the proximal end surface is an adhesive surface; and
    a main housing with a distal attachment surface formed by the distal end surface of the at least one attachment mechanism and a proximal actuation surface,
      wherein the proximal actuation surface defines an auxiliary injection user interface configured to apply pressure onto the injection user interface of the drug delivery device,
      wherein the proximal actuation surface comprises electrodes forming a capacitive switch.

8. The assembly according to claim 7, wherein the drug delivery device further comprises a clicker mechanism configured to generate an acoustic feedback signal at least during dose setting or dose dispensing.

9. The assembly according to claim 7, wherein the proximal actuation surface is an elastically deformable surface with a snap dome type switch positioned beneath the proximal actuation surface.

10. The assembly according to claim 7, wherein the main housing encases an electrical power source, a printed circuit board assembly, a sensor arrangement configured to detect a relative movement between at least two component parts of the drug delivery device, a communication unit for communicating with another device, and/or a switch arrangement.

11. The assembly according to claim 10, wherein the sensor arrangement is an acoustic sensor arrangement.

* * * * *